(12) United States Patent
Latt et al.

(10) Patent No.: US 11,285,031 B2
(45) Date of Patent: Mar. 29, 2022

(54) ACTIVE ASSIST ORTHOTIC

(71) Applicant: ARIZONA BOARD OF REGENTS ON BEHALF OF THE UNIVERSITY OF ARIZONA, Tucson, AZ (US)

(72) Inventors: L. Daniel Latt, Tucson, AZ (US); Michael Cameron Sveiven, Tucson, AZ (US); Blakeley Louise Koziol, Tucson, AZ (US); Carissa Liana Grijalva, Tucson, AZ (US); Justin Hsieh, Tucson, AZ (US); Adriana Barreda, Tucson, AZ (US); Timothy Shimon, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 340 days.

(21) Appl. No.: 16/610,262

(22) PCT Filed: Apr. 30, 2018

(86) PCT No.: PCT/US2018/030285
§ 371 (c)(1),
(2) Date: Nov. 1, 2019

(87) PCT Pub. No.: WO2018/820428
PCT Pub. Date: Nov. 8, 2018

(65) Prior Publication Data
US 2020/0146862 A1    May 14, 2020

Related U.S. Application Data

(60) Provisional application No. 62/492,760, filed on May 1, 2017.

(51) Int. Cl.
*A61F 5/01*    (2006.01)

(52) U.S. Cl.
CPC ...... *A61F 5/013* (2013.01); *A61F 2005/0155* (2013.01); *A61F 2005/0158* (2013.01)

(58) Field of Classification Search
CPC .......... A61F 5/0118; A61F 5/01; A61F 5/013; A61F 5/05858; A61F 5/05866;
(Continued)

(56) References Cited

U.S. PATENT DOCUMENTS 6,562,042 B2    5/2003    Nelson
7,416,537 B1    8/2008    Stark et al.
(Continued)

FOREIGN PATENT DOCUMENTS

CN    2524689    12/2002
CN    2857864    1/2007
(Continued)

OTHER PUBLICATIONS

Yih-Shiunn et al., Dynamic hip screw in the treatment of intertrochanteric fractures: a comparison of two fixation methods. Oct. 2007; 31(5): 683-688.
(Continued)

*Primary Examiner* — Tarla R Patel
(74) *Attorney, Agent, or Firm* — Nguyen Tarbet LLC

(57) ABSTRACT

An elbow brace is retrofitted to provide a motor-hinged orthotic elbow brace that stabilizes the elbow of a user and provides assisted motion to prevent or reduce buildup of scar tissue and maintain the range of motion of the elbow. A user interface is coupled to the brace for tracking exercises and the angle of the elbow brace. The orthotic elbow brace can also assist the patient in moving the arm at one or more predetermined angles according to physician instructions.

20 Claims, 9 Drawing Sheets

(58) Field of Classification Search
CPC .............. A61F 5/3723; A61F 5/373; A61F 2007/0029; A61F 2007/0034; A61F 2007/0035; A61F 2007/0036; A61F 2007/0037; A61F 2007/0038; A61F 13/10; A61F 5/37; A61F 2/54; A61F 2002/543; A61F 2002/546; A61F 2/583; A61F 2/585; A61F 2/586; A61F 2002/587; A61F 2/58; A61F 2005/0155; A61F 5/10; A61F 5/11; A61F 2007/0046; A61F 2007/0045; A61F 2013/00353; A61F 13/043; A61F 13/068; A61F 13/105; A61F 2002/6621; A61F 2002/6628

See application file for complete search history.

(56) References Cited

U.S. PATENT DOCUMENTS

| | | | |
|---|---|---|---|
| 7,927,333 | B2 | 4/2011 | Gradl |
| 2007/0050047 | A1* | 3/2007 | Ragnarsdottlr ....... A61F 2/6607 623/24 |
| 2008/0097269 | A1 | 4/2008 | Weinberg et al. |
| 2009/0227925 | A1* | 9/2009 | McBean ............... A61F 5/0127 602/16 |
| 2012/0165158 | A1* | 6/2012 | Ren ................. A63B 21/00178 482/7 |
| 2012/0209163 | A1 | 8/2012 | Phillips |
| 2013/0331744 | A1 | 12/2013 | Kamon |

FOREIGN PATENT DOCUMENTS

| | | |
|---|---|---|
| CN | 203089353 | 7/2013 |
| CN | 103393462 | 11/2013 |
| CN | 103126762 | 9/2015 |
| EP | 2626047 | 8/2013 |
| KR | 20100044358 A | 4/2010 |
| WO | 2017105996 A1 | 6/2017 |

OTHER PUBLICATIONS

Alobaid et al., Minimally Invasive Dynamic Hip Screw: Prospective Randomized Trial of Two Techniques of Insertion of a Standard Dynamic Fixation Device, J Orthop Trauma, Apr. 2004, vol. 18, No. 4.

Kyrylova, Development of a Wearable Mechatronic Elbow Brace for Postoperative Motion Rehabilitation, The University of Western Ontario, 2015.

Kim et al., Assistance of the elbow flexion motion on the active elbow orthosis using muscular stiffness force feedback, Journal of Mechanical Science and Technology, 25 (12) (2011) 3195~3203. www.springerlink.com/content/1738-494xDOI 10.1007/s12206-011-0923-9.

Rocon et al., Biomechanical Loading as an Alternative Treatment for Tremor: A Review of Two Approaches, Tremor and Other Hyperkinetic Movements, 2012, 1-13.

Sveiven et al., Active Elbow Orthosis Device, University of Arizona, The University of Arizona, 2017.

\* cited by examiner

ACTIVE ASSIST ORTHOTIC

CROSS REFERENCE

This application is a 371 and claims benefit of PCT/US18/30285 filed Apr. 30, 2018, which claims benefit of U.S. Provisional Application No. 62/492,760, filed May 1, 2017, the specification(s) of which is/are incorporated herein in their entirety by reference.

FIELD OF THE INVENTION

The present invention relates to an orthotic, more specifically, to a hinged brace having an active assistance mechanism that motorizes said hinge and provides active assistance to the wearer.

BACKGROUND OF THE INVENTION

Joint stiffness, such as elbow stiffness for example, is a common problem that is caused by the accumulation of fibrous tissue in the joint and surrounding structures during the healing process. It can occur after surgery or trauma (e.g. elbow dislocation), or can occur congenitally (e.g. arthrogryposis) or developmentally. It is made worse by the rigid bracing that is used to stabilize the elbow. It is commonly treated with range of motion exercises performed daily, but the exercises can be painful and are often ineffective. Hence, there is a need to solve this issue by simultaneously stabilizing the elbow while providing frequent motion.

One solution that can aid in stabilizing and moving a joint is the use of an active assist orthotic. An example of said orthotic is described in EP2626047 of Pohlig et al. The Pohlig orthotic comprises a motor that transmits a rotational movement to a worm shaft via a toothed belt drive. The worm shaft transmits the rotational movement in turn to an adjacent worm wheel, which transmits its rotary motion to a carrier disk, which in turn transmits the rotational movement to an output shaft via a clutch disk. With the rotational movement of the output shaft, a rail fixedly connected to the output shaft moves about the axis of rotation of the orthotic joint and against another rail, which is fixedly coupled to the base plate in the direction of rotation of the orthotic joint. The rails transmit this relative movement to each other on a first and second holding part, which are connected to a limb.

Another example of an active assist orthotic is disclosed by Kyrylova ("Development of a Wearable Mechatronic Elbow Brace for Postoperative Motion Rehabilitation", The University of Western Ontario, 2015). This orthotic comprises gears connecting support bars, a motor-gear box drive with a transmission system that allows the motor to be coupled and decoupled from the transmission system, a gear and pulley driver of the transmission system coupled to the gear of the support bars, a manually activated gear to engage motor to gear and pulley driver, and a control unit. An alternative mechanism for an active assist orthotic is described in Kim et al., ("Assistance of the elbow flexion motion on the active elbow orthotic using muscular stiffness force feedback", Journal of Mechanical Science and Technology, 25 (12) (2011) 3195-3203. www.springerlink.com/content/1738-494xDOI 10.1007/s12206-011-0923-9). Instead of being motor driven, the Kim orthotic relies on the action of artificial pneumatic muscles, which are operated by compressed air where raised air pressure contracts the muscles and lowered air pressure relaxes the muscles, to perform the basic movements of muscles, including flexion and extension.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide a motor-hinged joint brace that simultaneously stabilizes a joint and provides frequent motion to prevent the buildup of scar tissue and maintain the range of motion of the joint, as specified in the independent claims. Embodiments of the invention are given in the dependent claims. Embodiments of the present invention can be freely combined with each other if they are not mutually exclusive.

In some aspects, a hinged joint orthotic for stabilizing a hinge joint of a user while providing assistance during active flexion and extension movement of the joint is disclosed. Non-limiting examples of the hinge joint of the user include an elbow, knee, wrist, ankle, etc. While performing flexion and extension movement in the arm, the orthotic can actively assist the patient in moving the limb, e.g. arm or leg, to a predetermined angle. Without wishing to limit the invention to a particular theory or mechanism, the assisted flexion and extension movement of the joint effectively prevents stiffness or decreases stiffness associated with trauma or an underlying condition, while decreasing the chances of further injury.

In one embodiment, the present invention features an active assist hinged joint orthotic for providing active assistance for flexion or extension movement of a joint of a user to prevent or decrease joint stiffness. The flexion or extension movement may comprise a plurality of angles, where each angle is a specified degree formed by a limb having the joint as a vertex. In some embodiments, the active assist hinged joint orthotic may comprise a first alignment plate, a second alignment plate pivotably and operatively coupled to the first alignment plate via a hinge, a bevel gear disposed on the first alignment plate at or near the hinge, and a stepper motor disposed on the first alignment plate and aligned with the bevel gear. The stepper motor may have a motor shaft operatively coupled to the bevel gear which may be operatively coupled to the hinge.

In some embodiments, the first alignment plate and the second alignment plate are configured to be attached to a brace having the limb disposed therein, and the hinge may be positioned adjacent to the joint and preferably co-axial to the joint. Without wishing to limit the invention to a particular theory or mechanism, the alignment of the stepper motor and the bevel gear on the first alignment plate positions the stepper motor away from the affected joint and closer to a center of the limb and to a center of the user's body, thus reducing an apparent weight of the orthotic experienced by the user. In some embodiments, the stepper motor can apply a torque to the bevel gear, which transfers said torque to a gear shaft of the bevel gear. Thus, rotation of the gear shaft drives rotation of the hinge, which moves the first alignment plate and the second alignment plate into a position reflecting the selected angle. The brace moves simultaneously with the movement of the plates, thereby positioning the limb at the selected angle.

In other embodiments, the active assist hinged joint orthotic may further comprise a gearbox that houses the bevel gear. In other embodiments, the active assist hinged joint orthotic may further comprise a clutch operatively coupling the motor shaft to the bevel gear. If the limb of the user applies a resistance that opposes the movement of the brace and thus the hinge, which can potentially lead to an opposing torque transfer damaging the stepper motor, then the clutch is configured to release the motor shaft to allow the motor shaft to maintain its torque, and the opposing torque transferred to the bevel gear is not experienced by the stepper motor as a result of said clutch release.

In some other embodiments, the active assist hinged joint orthotic may further comprise a bipolar stepper motor driver operatively coupled to the stepper motor. A microcontroller may be operatively coupled to the bipolar stepper motor driver, which activates the bipolar stepper motor driver to drive the stepper motor a number of motor steps required to position the brace at the selected angle. A memory repository may also be operatively coupled to the microcontroller. The memory repository can store instructions comprising the number of motor steps required to position the active assist hinged joint orthotic at each angle or an exercise regimen comprising a series of angles to be executed by the user with aid from the active assist hinged joint orthotic.

According to other aspects, the present invention features an active assist elbow orthotic for stabilizing an elbow of a user while providing active assistance for flexion or extension movement of an arm of the user to prevent stiffness or decrease stiffness of the elbow. The elbow orthotic may comprise an elbow brace that stabilizes the elbow and an active assist mechanism that provides assistance to the user as the user exerts effort to move the arm to a selected elbow angle. In some embodiments, the elbow brace may comprise an upper component operatively coupled to a lower component via a first hinge. The elbow brace is configured to be worn on the arm such that an upper arm is disposed in the upper component, a forearm is disposed in the lower component, and the first hinge is adjacent to the elbow. The first hinge permits flexion or extension movement of the arm from the elbow, which can comprise a plurality of elbow angles, each elbow angle being a specified degree formed by the elbow.

In other embodiments, the active assist mechanism may comprise a first alignment plate operatively coupled to the upper component of the elbow brace, a second alignment plate operatively coupled to the lower component of the elbow brace and pivotably coupled to the first alignment plate via a second hinge co-axial with the first hinge and elbow, a bevel gear disposed on the first alignment plate at or near the hinge and operatively coupled to the hinge, and a stepper motor disposed on the first alignment plate and aligned with the bevel gear. The stepper motor can have a motor shaft operatively coupled to the bevel gear. Preferably, the alignment of the stepper motor and the bevel gear on the first alignment plate positions the stepper motor away from the affected elbow joint and closer to a center of the arm and to a center of the user's body, thus reducing an apparent weight of the orthotic experienced by the user. The stepper motor is configured to apply a torque to the bevel gear, which transfers said torque to a gear shaft of the bevel gear. Rotation of the shaft drives rotation of the second hinge, thereby moving the first alignment plate and the second alignment plate into a position reflecting a selected angle of the plurality of elbow angles. The elbow brace moves simultaneously with the movement of the plates, thus positioning the arm at the selected angle.

In some embodiments, the active assist mechanism may further comprise a gearbox that houses the bevel gear. In other embodiments, the active assist mechanism may further comprise a DC power supply to power the stepper motor. In still other embodiments, the active assist mechanism may further comprise a clutch operatively coupling the motor shaft to the bevel gear such that rotation of the bevel gear is synchronized to a rotation of the motor shaft. In preferred embodiments, if the user applies a resistance that opposes the movement of the brace and thus the hinge, which can potentially lead to an opposing torque transfer damaging the stepper motor, then the clutch is configured to release the motor shaft to allow the motor shaft to maintain its torque and the opposing torque transferred to the bevel gear is not experienced by the stepper motor as a result of said clutch release.

In other embodiments, the active assist mechanism may further comprise a bipolar stepper motor driver operatively coupled to the stepper motor. A microcontroller may be operatively coupled to the bipolar stepper motor driver and activates the driver to drive the stepper motor the number of motor steps required to position the elbow brace at a selected elbow angle. The stepper motor then applies a torque to the clutch and consequently to the bevel gear, which applies the torque to the gear shaft. In other embodiments, a first memory repository may be operatively coupled to the microcontroller for storing instructions comprising the number of motor steps required to position the elbow brace at each elbow angle. In still other embodiments, a first transceiver may also be operatively coupled to the microcontroller and wirelessly coupled to a second transceiver. The second transceiver may be operatively coupled to a display interface that receives an input indicating the selected elbow angle. The second transceiver wirelessly sends the input to the first transceiver for subsequent transmission to the microcontroller, which activates the bipolar stepper motor driver to ultimately rotate the second hinge and move the alignment plates, and correspondingly the elbow brace, into the position reflecting the selected elbow angle.

In additional embodiments, the input may be an exercise regimen comprising a series of elbow angles to be executed by the user within a given time period while being assisted by the active assist mechanism. The given time period may be clocked by a timer operatively coupled to the display interface. In another embodiment, the display interface may be operatively coupled to a second memory repository that stores the exercise regimen.

In further embodiments, a potentiometer may be coupled to the microcontroller. The potentiometer can determine a degree of an elbow angle based on a position of the elbow brace. The potentiometer can collect data comprising the degree of each elbow angle formed by the arm of the user and transmit said data to the microcontroller for transmission, via the first transceiver, to the second transceiver. The second transceiver can then send the data to the display interface for display and subsequent storage in the second memory repository.

In still further embodiments, the active assist mechanism may further comprise a locking mechanism disposed on the elbow brace adjacent to the first hinge for locking the elbow brace in a desired position. The locking mechanism may comprise an inner tube having a spring disposed therein, a pin operatively coupled to a first end of the inner tube, and a conical tip operatively coupled to a second end of the inner tube. When the pin is pressed, the pin compresses the spring and locks in place, said spring compression thrusts the conical tip into a gear disposed within the first hinge, thereby preventing the gear, and thus the elbow brace, from rotating. The pin is pressed again to release the pin from its locked configuration, which causes the pin to retract from the inner tube, thereby releasing the spring and causing retraction of the conical tip, thereby freeing the gear and the elbow brace to allow rotation thereof.

One of the unique and inventive technical features of the present invention is the alignment of the stepper motor and the bevel gear on the first alignment plate. As used herein, the bevel gear comprises two rotating gears oriented such that their rotational axes intersect at a 90° angle. As shown in FIG. 2, the first rotating gear is disposed on the first alignment plate at the hinge and co-axial with the gear shaft. The second rotating gear is also disposed on the first alignment plate and perpendicular to the first rotating gear. Thus, the second rotating gear is aligned with the stepper motor. Without wishing to limit the invention to any theory or mechanism, it is believed that this configuration advantageously allows for the stepper motor to be positioned closer to the center of body, e.g. on the upper arm and closer to the shoulder, which reduces the apparent weight of the orthotic experienced by the user. The resistance to rotational acceleration, also known as rotational inertia or angular mass, increases by the square of the distance of a mass from the center of rotation, thus by placing a mass closer to the center of rotation, this decreases the apparent weight that is felt by the user. In the present invention, the weight of the motor is near the center of rotation of the shoulder and of the upper arm. Moreover, the weight of the device is more evenly distributed along the upper arm, which further reduces the apparent weight of the device. Another advantage of this configuration is that it eliminates the need for gear belts and pulleys thereby further reducing the weight of orthotic. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which.

DETAILED DESCRIPTION OF THE INVENTION

Figure 1:
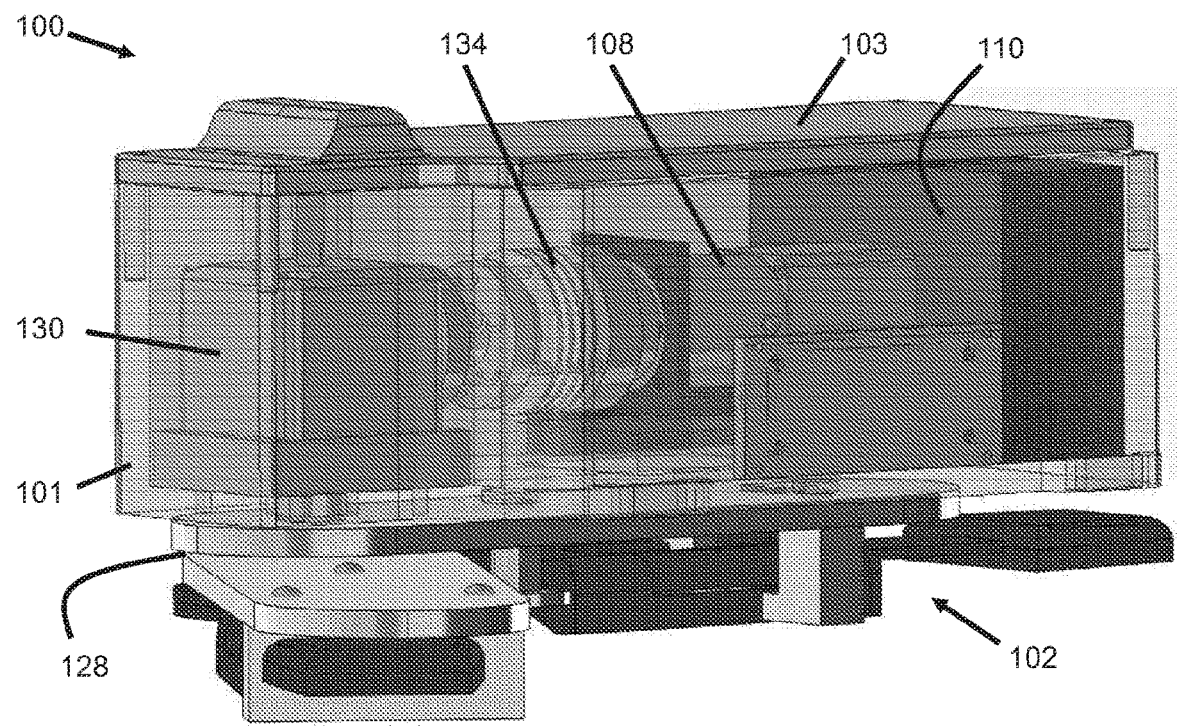
FIG. 1 shows an active assist orthotic of the present invention assembled and enclosed in the active assist mechanism case.
Figure 2:
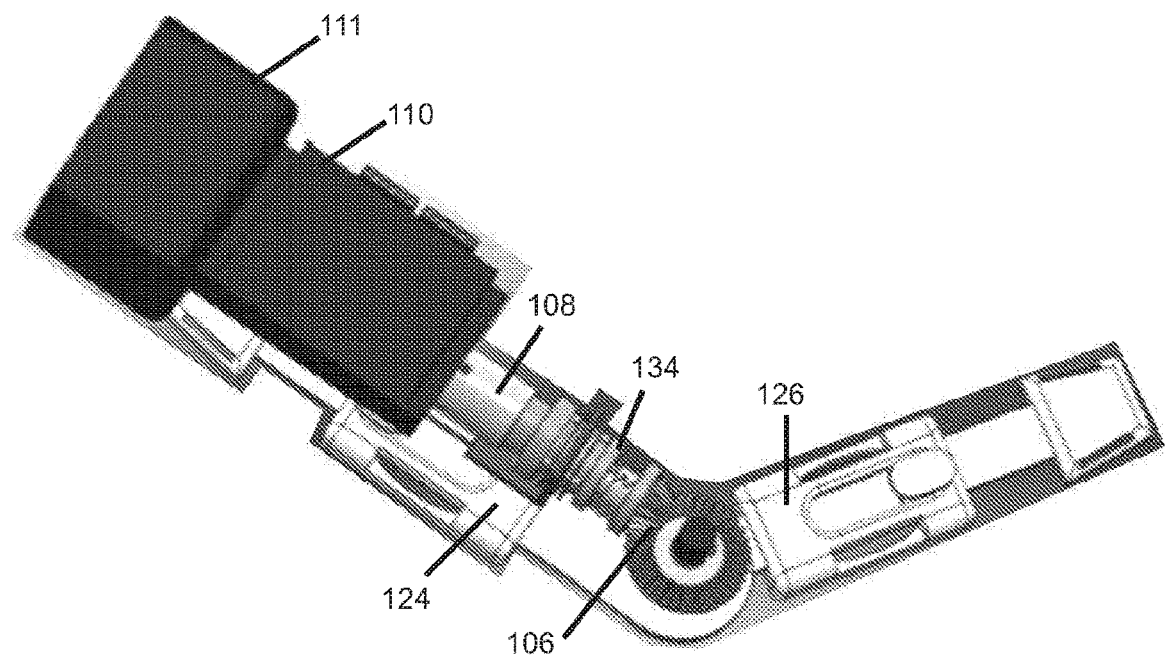
FIG. 2 shows a top view of the active assist orthotic.
Figure 3A:
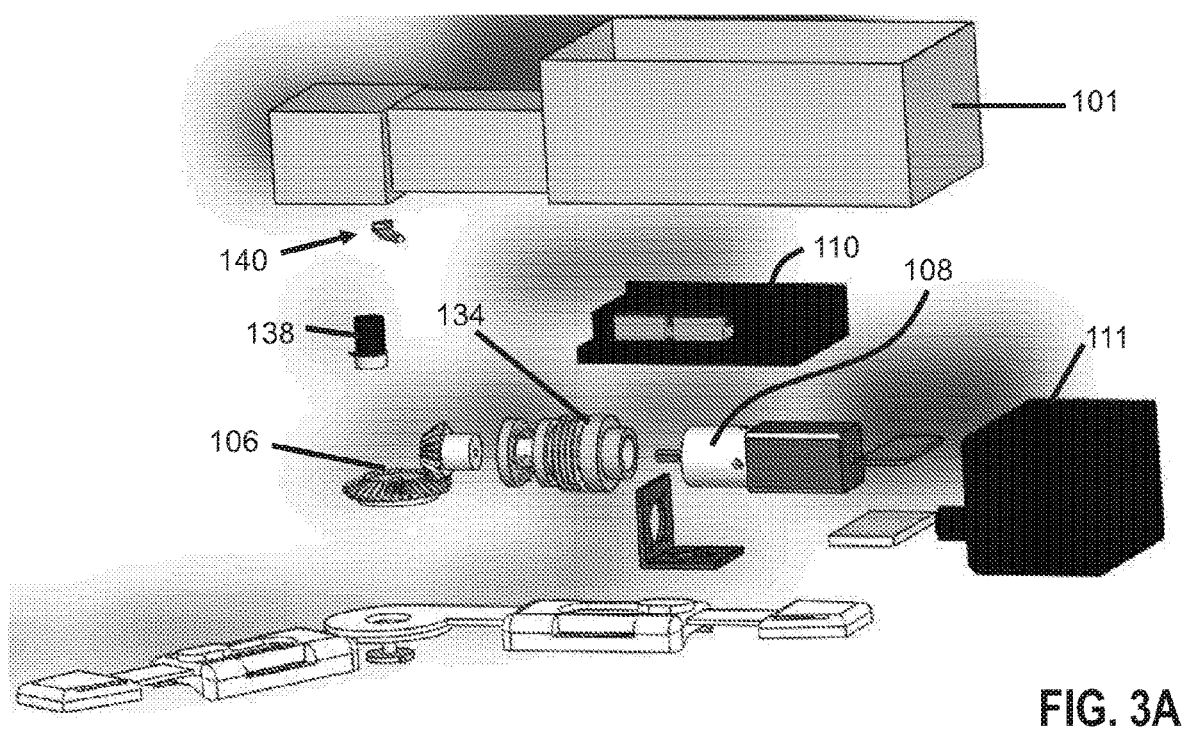
FIGS. 3A-3B show exploded views of the active assist mechanism including: a stepper motor, potentiometer, clutch, microcontroller, pinion bevel, bevel gear, motor driver, shaft, batteries, elbow brace, motor mounting bracket, emergency stop and case.
Figure 3B:
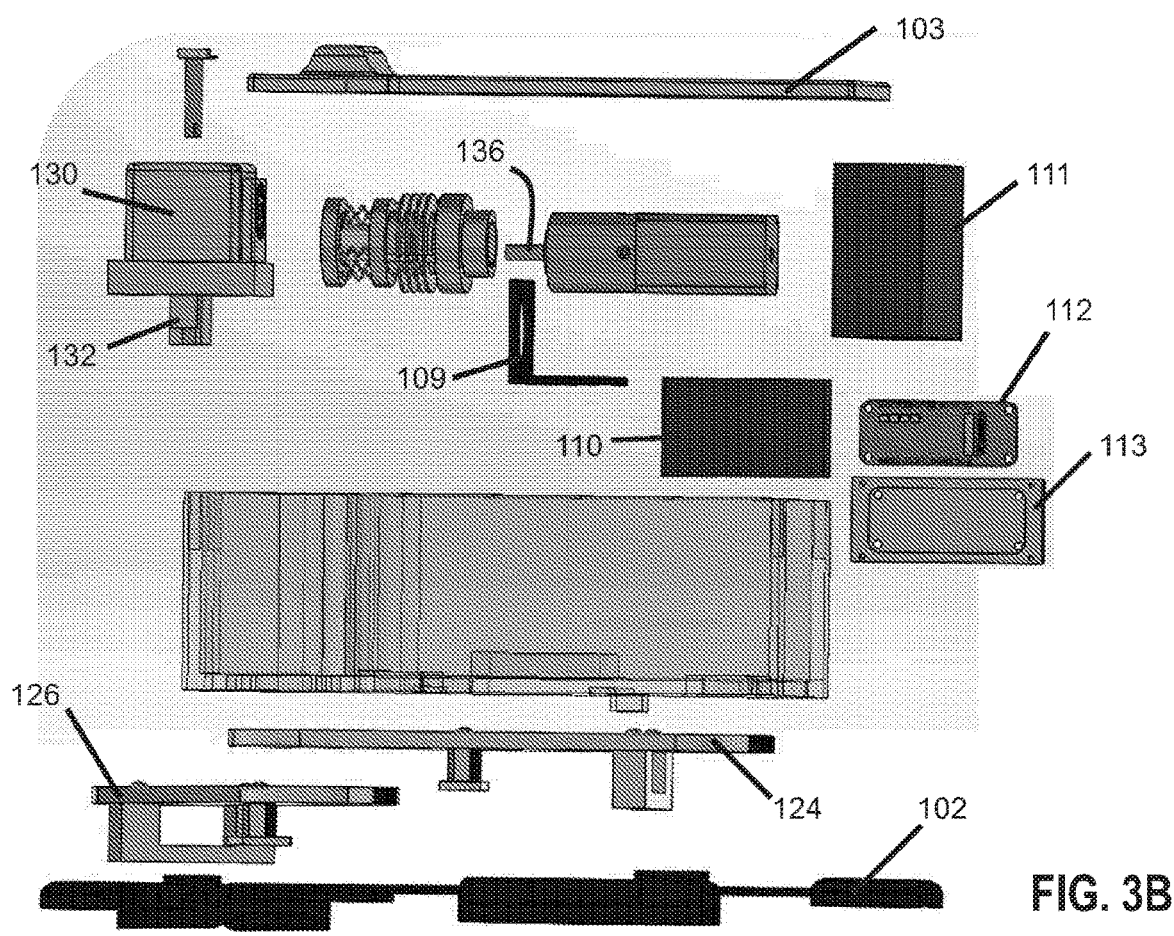
Figure 4A:
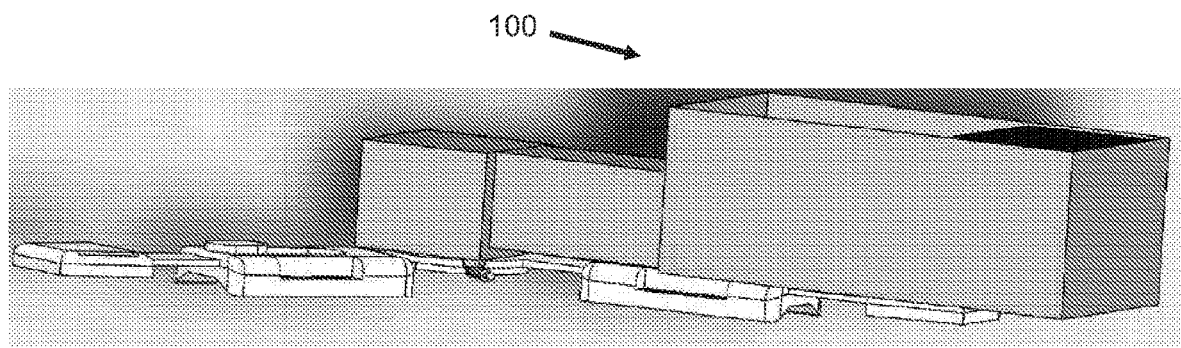
FIGS. 4A-4B show the active assist orthotic with the active assist mechanism case.
Figure 4B:
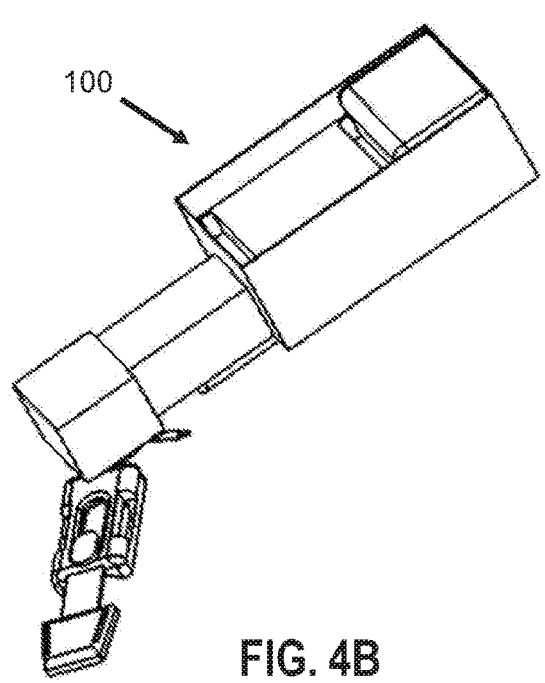
Figure 4C:
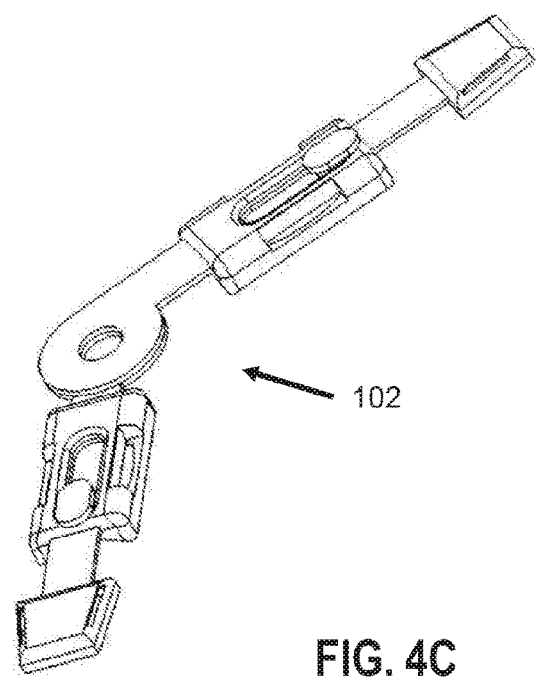
FIGS. 4C-4D show non-limiting embodiments of an elbow brace.
Figure 4D:
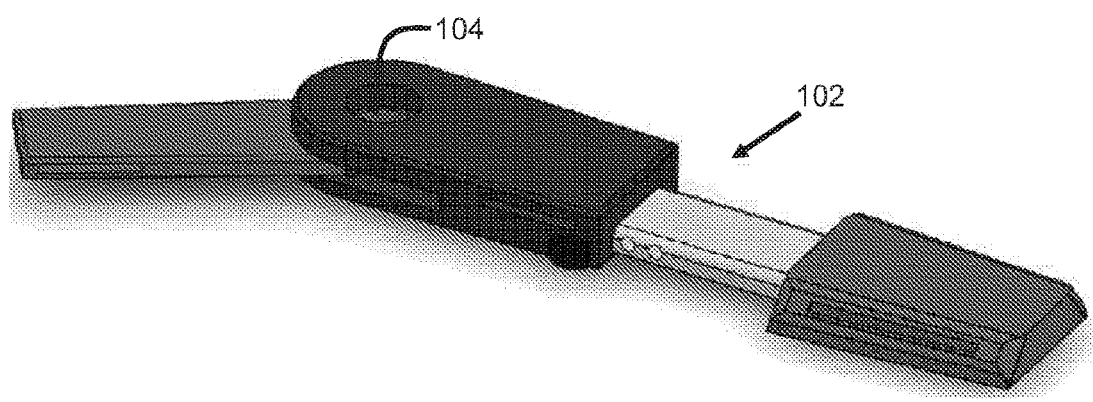
Figure 5A:
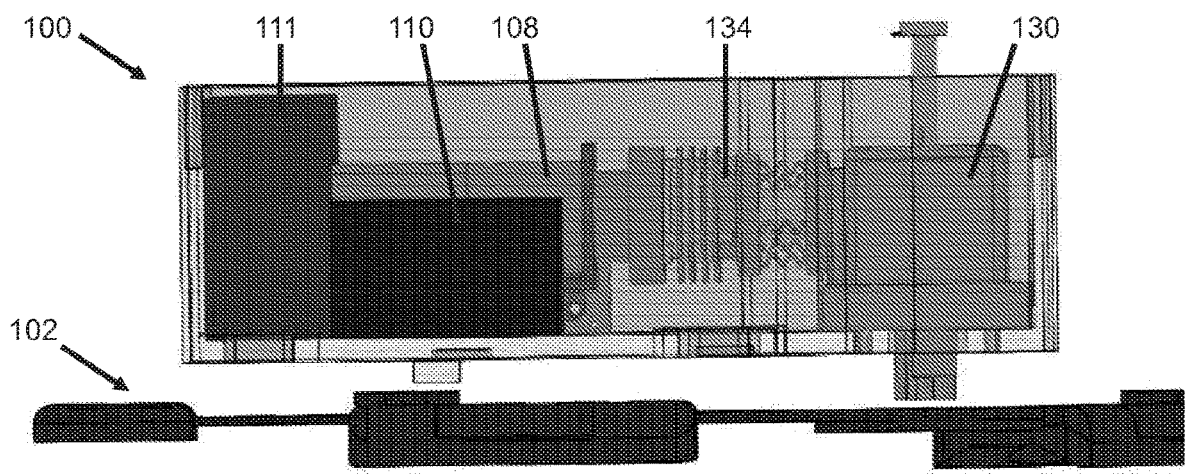
FIG. 5A shows a side view of the active assist mechanism.
Figure 5B:
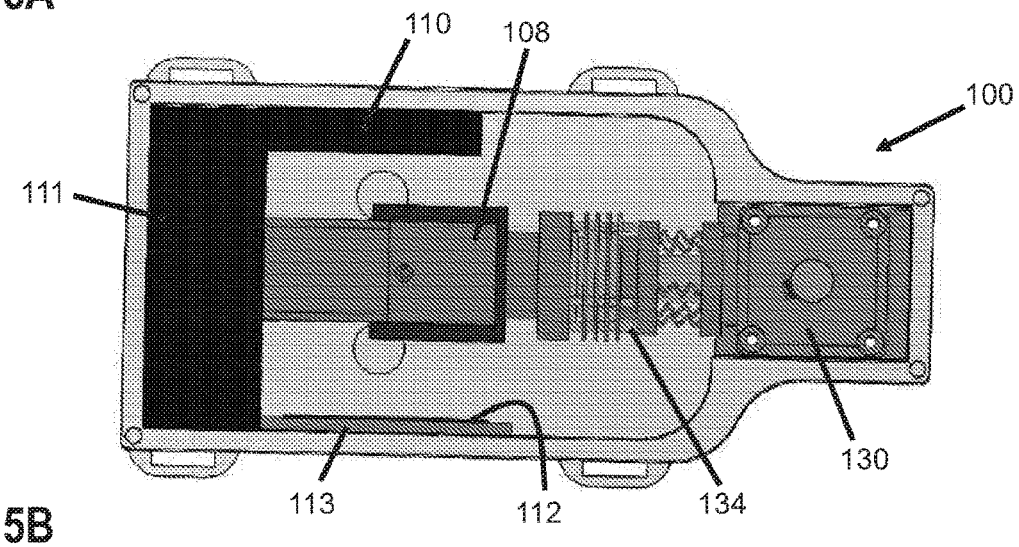
FIG. 5B shows a top view of the active assist mechanism.
Figure 5C:
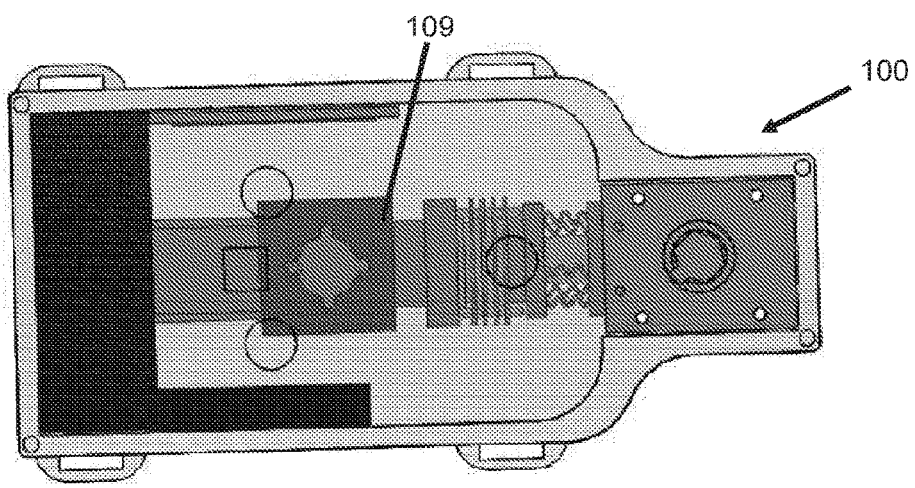
FIG. 5C shows a bottom view of the active assist mechanism.
Figure 6A:
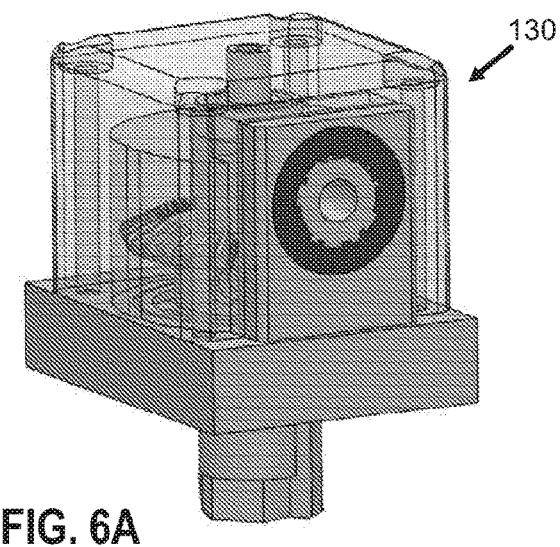
FIG. 6A shows a perspective view of a bevel gear in a gear box.
Figure 6B:
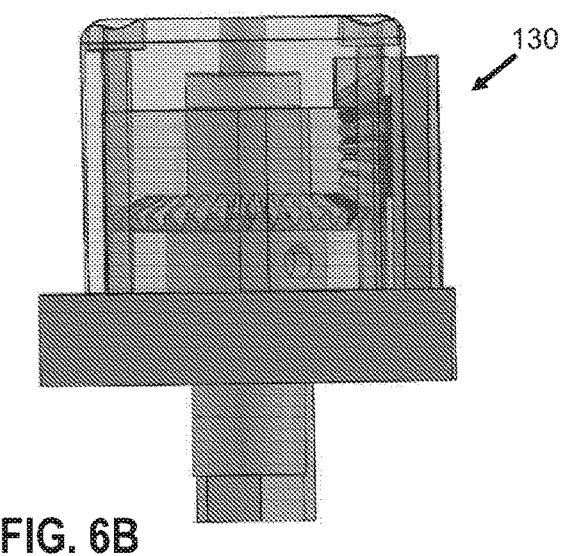
FIG. 6B shows a side view of a bevel gear in a gear box.
Figure 7A:
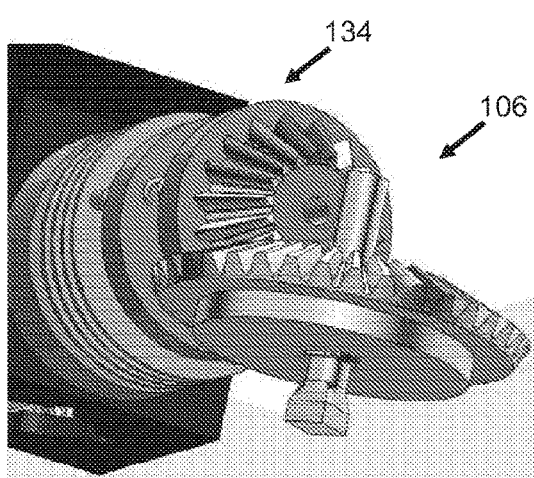
FIGS. 7A-7B show perspective views of the bevel gear.
Figure 7B:
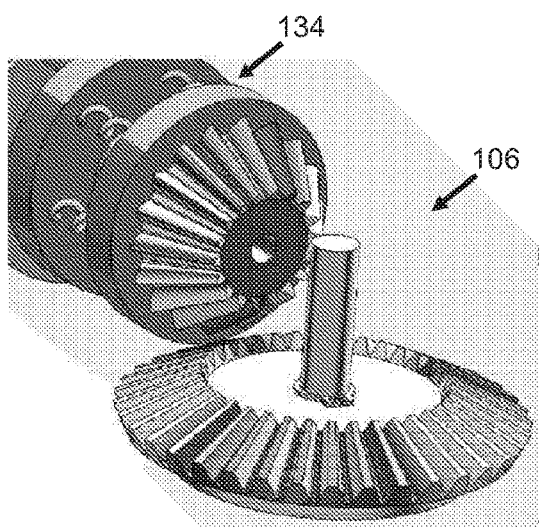
Figure 7C:
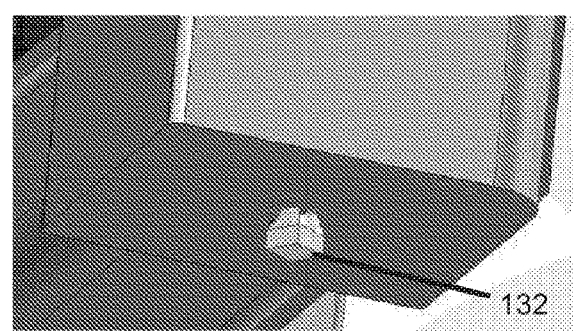
FIG. 7C shows a shaft having a square shape to allow the join between the elbow brace and motor allowing for the rotation of only the forearm extension.

Following is a list of elements corresponding to a particular element referred to herein:
100 Active assist mechanism
101 Active assist mechanism case
102 Elbow brace
103 Case top
104 First hinge
106 Bevel gear
108 Stepper motor
109 Motor mount
110 Stepper motor driver
111 DC power supply
112 Microcontroller
113 Microcontroller mount
114 First memory repository
116 First transceiver
118 Display interface
120 Second transceiver
122 Second memory repository
124 First alignment plate
126 Second alignment plate
128 Second hinge
130 Gearbox
132 Shaft
134 Clutch
136 Motor shaft
138 Potentiometer
140 Locking mechanism
142 Inner tube
144 Pin
146 Conical tip As used herein, the term "flexion" refers to a bending movement decreasing an angle formed between an upper arm, a forearm, and the adjoining elbow. As used herein, the term "extension" refers to a straightening movement increasing an angle formed between an upper arm, a forearm, and the adjoining elbow.

Referring now to FIGS. 1-12, the present invention features a hinged joint orthotic system for stabilizing a hinge joint of a user while providing active assistance for flexion and extension movement of the joint. Non-limiting examples of the hinge joint of the user include: an elbow, knee, wrist, ankle, etc. The assisted flexion and extension movement of the joint effectively prevents stiffness or decreases stiffness associated with trauma or an underlying condition, while decreasing the chances of further injury. In some embodiments, the system comprises an elbow brace (102) having an upper component operatively coupled to a lower component, via a first hinge (104). The arm of the user is disposed within the elbow brace (102) such that the upper arm is disposed in the upper component and the forearm is disposed in the lower component. The first hinge permits flexion and extension movement of the arm of the user from the elbow. In other embodiments, flexion or extension movement may comprise a plurality of elbow angles, where an elbow angle of a specified degree is formed by a position of an upper arm relative to a position of a forearm having an adjoining elbow as a vertex.

In further embodiments, the system also comprises an active assist mechanism (100) having a first alignment plate (124) and a second alignment plate (126) operatively coupled together via a second hinge (128). In an embodiment, the first alignment plate (124) is operatively coupled to the upper component of the elbow brace (102), while the second alignment plate (126) is operatively coupled to the lower component of the elbow brace (102). A gearbox (130), having a gearbox top end and a gearbox bottom end, and a shaft (132), having a shaft top end and a shaft bottom end, may also comprise the active assist mechanism (100). In one embodiment, the shaft top end is operatively coupled to the gearbox (130) bottom end and the shaft bottom end is operatively coupled to the second hinge (128). In another embodiment, the gearbox (130) houses a bevel gear (106).

In additional embodiments, a shaft (132), having a shaft top end and a shaft bottom end, may further comprise the active assist mechanism. The shaft top end may be operatively coupled to the gearbox (130) bottom end, while the shaft bottom end may be operatively coupled to the second hinge (128). A clutch (134), having a clutch first side and a clutch second side, may be operatively coupled to the bevel gear (106) via the clutch second side. A stepper motor (108), having a motor first side and a motor second side, may be operatively coupled to a motor shaft (136) via the motor second side. Further, the motor shaft (136) may couple the motor second side to the clutch first side. In some embodiments, the clutch (134) synchronizes the speed of the bevel gear (106) to the speed of the stepper motor (108). In other embodiments, a bipolar stepper motor driver (110) is operatively coupled to the motor first side.

In supplementary embodiments, a microcontroller (112) is operatively coupled to both the bipolar stepper motor driver (110) and to a first memory repository (114). In one embodiment, first memory repository (114) stores instructions comprising a number of motor steps required to position the elbow brace (102) to each elbow angle of the plurality of elbow angles comprising flexion and extension movement.

Consistent with previous embodiments, the microcontroller (112) activates the bipolar stepper motor driver (110) to drive the stepper motor (108) the number of motor steps required to position the elbow brace (102) at a selected elbow angle. As the motor second side is coupled to the clutch first side, the driving force applied to the stepper motor transfers a torque to the clutch (134) and subsequently to the bevel gear (106). Since the stepper motor (108) and the clutch (134) are positioned horizontally, the bevel gear (106) operates to transfer the torque from the horizontal axis to the vertical axis. The torque, now at the vertical axis, is transferred to the shaft (132) via the bevel gear (106). Rotation of the shaft (132) then drives rotation of the second hinge (128) the required number of motor steps, which moves the first alignment plate (124) and the second alignment plate (126) into a position reflecting the selected elbow angle. As the first alignment plate (124) and the second alignment plate (126) move, the upper component and the lower component of the elbow brace (102) moves correspondingly such that the elbow brace also reflects the position of the selected elbow angle.

In some cases, the user will resist the movement of the elbow brace (102) (e.g. because of increasing, unbearable, or unnatural pain). If this occurs, the arm of the user is effectively applying an opposing force to both the elbow brace (102) and to the second hinge (128). As the second hinge (128) is coupled to the shaft (132), this opposing force (i.e. torque) may ultimately lead to an opposing torque transfer damaging to the stepper motor (108). Therefore, in this situation, the clutch (134) will release the motor shaft (136) to allow the motor shaft (136) to maintain the torque being applied by the bipolar stepper motor driver (110). Thus the opposing torque, which is transferred to the bevel gear (106) via the shaft (132), is not experienced by the stepper motor (108) as a result of said clutch release.

In further embodiments, the system may also comprise a display interface (118) and a second transceiver (120) operatively coupled to the display interface (118). In one embodiment, the display interface (118) may be a graphical user interface ("GUI") configured to receive input from and display information to a user. In a further embodiment, the GUI may take the form of a software application downloaded to a user electronic device.

Input may comprise the selected elbow angle or an exercise regimen comprising a series of elbow angles to be executed by the user aided by the active assist mechanism (100). In another embodiment, an authorized party (e.g. the user's doctor) may provide the input to the display interface (118). The input is wirelessly sent from the second transceiver (120) to a first transceiver (116) operatively coupled to the microcontroller (112). The first transceiver (116) then transmits the input to the microcontroller (112), which activates the bipolar stepper motor driver (110) to ultimately move the active assist mechanism (100), and correspondingly the elbow brace (102), into the position reflecting the selected elbow angle. As the active assist mechanism (100) moves into the position, the user exerts effort to move the arm to the selected elbow angle with active assistance from the elbow brace (102) via the active assist mechanism (100).

In some embodiments, a DC power supply (111) (e.g. a battery) powers the bipolar stepper motor driver (110) and motor (108). In other embodiments, a lithium ion battery powers the microcontroller.

In other embodiments, the exercise regimen is to be executed by the user within a given time period, which is clocked by a timer operatively coupled to the display interface (118). A second memory repository (122), also coupled to the display interface (118), may store the exercise regimen comprising the series of elbow angles to be executed and the given time period for execution.

In additional embodiments, the system may further comprise a potentiometer (138) operatively coupled to both the gearbox top end and to the microcontroller (112). The potentiometer (138) may determine a degree of an elbow angle based on a position of the elbow brace (102). As the user executes the exercise regimen, the potentiometer (138) may collect data, comprising a degree of each elbow angle formed by the arm of the user, and transmit said data to the microcontroller (112). The first transceiver (116) may then transmit the data to the second transceiver (120) for display via the display interface (118). The data may also be stored in the second memory repository (122).

In supplementary embodiments, a locking mechanism (140) may be disposed on the elbow brace (102) adjacent to the first hinge (104) for locking the elbow brace (102) in a desired position. In some embodiments, the locking mechanism (104) comprises an inner tube (142) having a spring disposed therein, a pin (144) operatively coupled to a first end of the inner tube (142), and a conical tip (146) operatively coupled to a second end of the inner tube (142) (see FIG. 8). When the user applies a first compressive force to the pin (144), the pin (144) compresses the spring and locks in place. The spring compression applies a force to the conical tip (146) thrusting the conical tip (146) into a gear disposed within the first hinge (104) to prevent the gear, and thus the elbow brace (102), from rotating. When a subsequent second compressive force is applied to the pin (144), the pin (144) retracts from the inner tube (142) releasing the spring. Once the spring is released, the conical tip (146) retracts from the gear and into the inner tube (142) thus freeing the gear and the elbow brace (102) to rotate.

The present invention additionally features a retrofit device, herein referred to as an active assist hinged joint orthotic, providing active assistance to a user while performing flexion or extension movements of a limb, thus effectively preventing or decreasing stiffness associated with trauma or an underlying condition. Non-limiting examples of the hinge joint include: an elbow, knee, wrist, ankle, etc. Flexion and extension movements comprise a plurality of angles, where each angle is of a specified degree formed by the limb having the joint as a vertex. In some embodiments, the active assist hinged joint orthotic comprises a first alignment plate (124) and a second alignment plate (126) operatively coupled to the first alignment plate (124) via a hinge (128).

In some embodiments, the active assist hinged joint orthotic may comprise a gearbox (130) having a gearbox top end and a gearbox bottom end, and a shaft (132) having a shaft top end and a shaft bottom end. In one embodiment, the shaft top end is operatively coupled to the gearbox (130) bottom end and the shaft bottom end is operatively coupled to the hinge (128). In another embodiment, the gearbox (130) houses a bevel gear (106).

In additional embodiments, a clutch (134), having a clutch first side and a clutch second side, may be operatively coupled to the bevel gear (106) via the clutch second side. A stepper motor (108), having a motor first side and a motor second side, may be operatively coupled to a motor shaft (136) via the motor second side. Further, the motor shaft (136) may couple the motor second side to the clutch first side. In some embodiments, the clutch (134) synchronizes the speed of the bevel gear (106) to the speed of the stepper motor (108). In other embodiments, a bipolar stepper motor driver (110) is operatively coupled to the motor first side.

In supplementary embodiments, a microcontroller (112) is operatively coupled to both the bipolar stepper motor driver (110) and to a memory repository. In one embodiment, the memory repository stores instructions comprising a number of motor steps required to position the active assist hinged joint orthotic at each angle, of the plurality of elbow angles comprising flexion and extension movement. In exemplary embodiments, the active assist hinged joint orthotic is coupled to a brace having the limb disposed therein. Non-limiting examples of the brace include: an elbow brace, knee brace, wrist brace, ankle brace, or any commercially available brace.

Consistent with previous embodiments, the microcontroller (112) activates the bipolar stepper motor driver (110) to drive the stepper motor (108) the number of motor steps required to position the brace at a selected angle. As the motor second side is coupled to the clutch first side, the driving force applied to the stepper motor transfers a torque to the clutch (134) and subsequently to the bevel gear (106). Since the stepper motor (108) and the clutch (134) are positioned horizontally, the bevel gear (106) operates to transfer the torque from the horizontal axis to the vertical axis. The torque, now at the vertical axis, is transferred to the shaft (132) via the bevel gear (106). Rotation of the shaft (132) then drives rotation of the second hinge (128) the required number of motor steps, which moves the first alignment plate (124) and the second alignment plate (126) into a position reflecting the selected angle. As the first alignment plate (124) and the second alignment plate (126) move, the brace moves correspondingly such that the brace also reflects the position of the selected angle.

In some cases, the user will resist the movement of the brace (e.g. because of increasing, unbearable, or unnatural pain). If this occurs, the limb of the user is effectively applying an opposing force to both the brace and to the hinge (128). As the hinge (128) is coupled to the shaft (132), this opposing force (i.e. torque) may ultimately lead to an opposing torque transfer damaging to the stepper motor (108). Therefore, in this situation, the clutch (134) will release the motor shaft (136) to allow the motor shaft (136) to maintain the torque being applied by the bipolar stepper motor driver (110). Thus the opposing torque, which is transferred to the bevel gear (106) via the shaft (132), is not experienced by the stepper motor (108) as a result of said clutch release.

Since it has been described an active assistance orthotic, it is another objective of the present invention to provide active assistance to a limb of a user. Thus, in some embodiments, the present invention features a method for providing active assistance to an arm of a user performing flexion or extension movement in order to prevent or decrease stiffness of an elbow joint.

In one embodiment, the method may comprise providing any one of the orthotics described herein, installing the elbow brace (102) onto the arm such that an upper arm is disposed in the upper component, a forearm is disposed in the lower component, and the first hinge (104) is adjacent to the elbow, and driving the stepper motor (106) a number of motor steps required to position the elbow brace (102) at a selected elbow angle of the plurality of elbow angles, thus applying a torque to the bevel gear (106) via a motor shaft (136), which transfers said torque to a gear shaft (132) of the bevel gear. Rotation of the shaft (132) drives rotation of the second hinge (128), thereby moving the first alignment plate (124) and the second alignment plate (126) into a position reflecting the selected angle. The elbow brace (102) moves simultaneously with the movement of the plates to position the arm at the selected angle, thus the active assist mechanism (100) assists the user as the user exerts effort to move the arm to the selected elbow angle.

In some preferred embodiments, a clutch (134) may operatively couple the motor shaft (136) to the bevel gear (106) such that rotation of the bevel gear (106) is synchronized to a rotation of the motor shaft (136). If the user applies a resistance that opposes the movement of the elbow brace (102), and thus the hinge (128), this may potentially cause an opposing torque transfer that can damage the stepper motor (108). The clutch (134) can prevent the motor from being damaged by releasing the motor shaft (136) to allow the motor shaft (136) to maintain its torque and the opposing torque transferred to the bevel gear (106) is not experienced by the stepper motor (108) as a result of said clutch release.

In some embodiments, a bipolar stepper motor driver (110) may be operatively coupled to the stepper motor (108) for driving the stepper motor (108). A microcontroller (112) may be operatively coupled to the bipolar stepper motor driver (110). A first memory repository (114) may be operatively coupled to the microcontroller (112) and stores instructions comprising the number of motor steps required to position the elbow brace (102) at each elbow angle. The microcontroller (112) can activate the bipolar stepper motor driver (110) to drive the stepper motor (108) the number of motor steps required to position the elbow brace (102) at the selected elbow angle, thus applying a torque to the clutch (134) and consequently to the bevel gear (106), which applies the torque to the gear shaft (132) and the hinge.

Example

Without wishing to limit the present invention to any particular embodiment, the following is a description of example components comprising the active assist elbow orthotic of the present invention. Equivalents or substitutes are within the scope of the invention.

In preferred embodiments, the motor-hinged elbow orthotic can maintain as much range of motion in the joint throughout a healing process while also breaking down the scar tissue in the joint. The device can aid recovery after surgery and has the advantage over physical therapy of being wearable and user controllable. While performing the flexion/extension movement in the arm, the orthotic can actively assist the patient into moving the arm to a predetermined angle as prescribed by a physician.

In one embodiment, the active assist elbow orthotic system is broken up into two main distinctions: the arm brace including the mechanical and electrical components and the display interface (118), herein referred to an iOS® application. The arm brace may comprise a Breg T Scope Elbow Premier®, an Arduino® MKR1000, a Nema 11® Stepper Motor, a Bipolar Stepper Motor Driver, a Dynatect® SAS20 clutch, a 5K ohm potentiometer (sensor), locking pin, and a power supply consisting of a lithium ion polymer battery and a 19.2 volt battery. The iOS® application can include pages for login, schedule calendar of exercises, exercise history, and exercise initiation.

The iOS® application can interface with the patient-user. Instructions for use of the iOS® application may be provided in a Technical Data Package. The iOS® application can connect through Wi-Fi with the Arduino®. The Arduino® can send the application information on the angle of the elbow brace and the application can process and store that information. Based on the application exercise schedule, the application sends instructions to the Arduino® on when and to what extent the motor will act in assisting elbow flexion or extension.

Figures 9A, 9B:
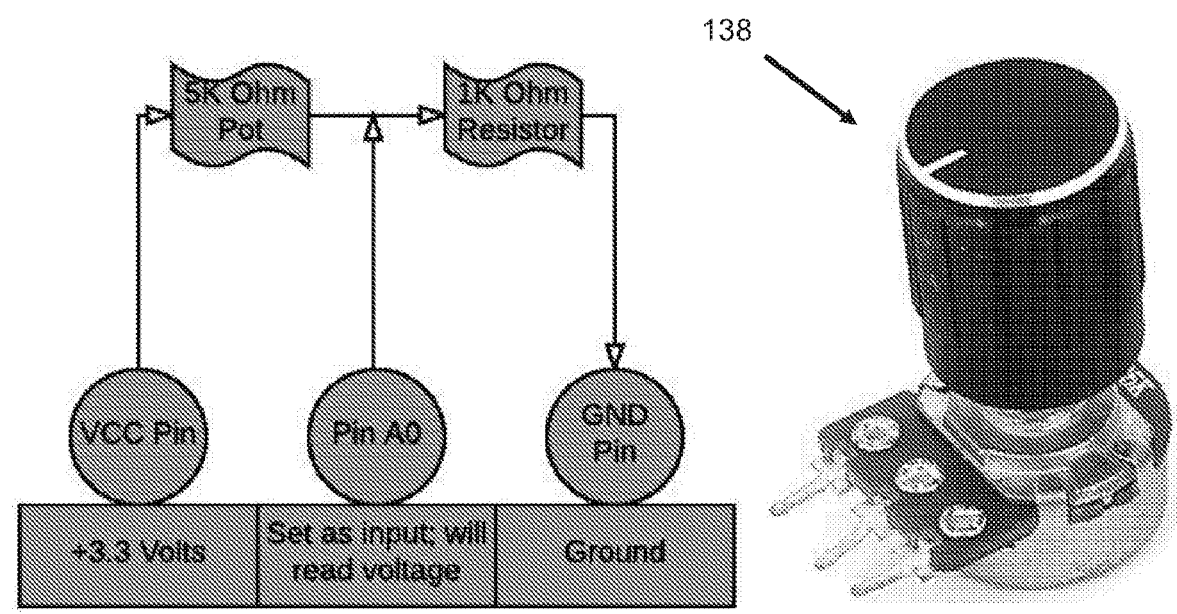
FIG. 9A shows a diagram of the potentiometer interfacing with the microcontroller.
FIG. 9B shows a prototype of the potentiometer.
Figure 10:
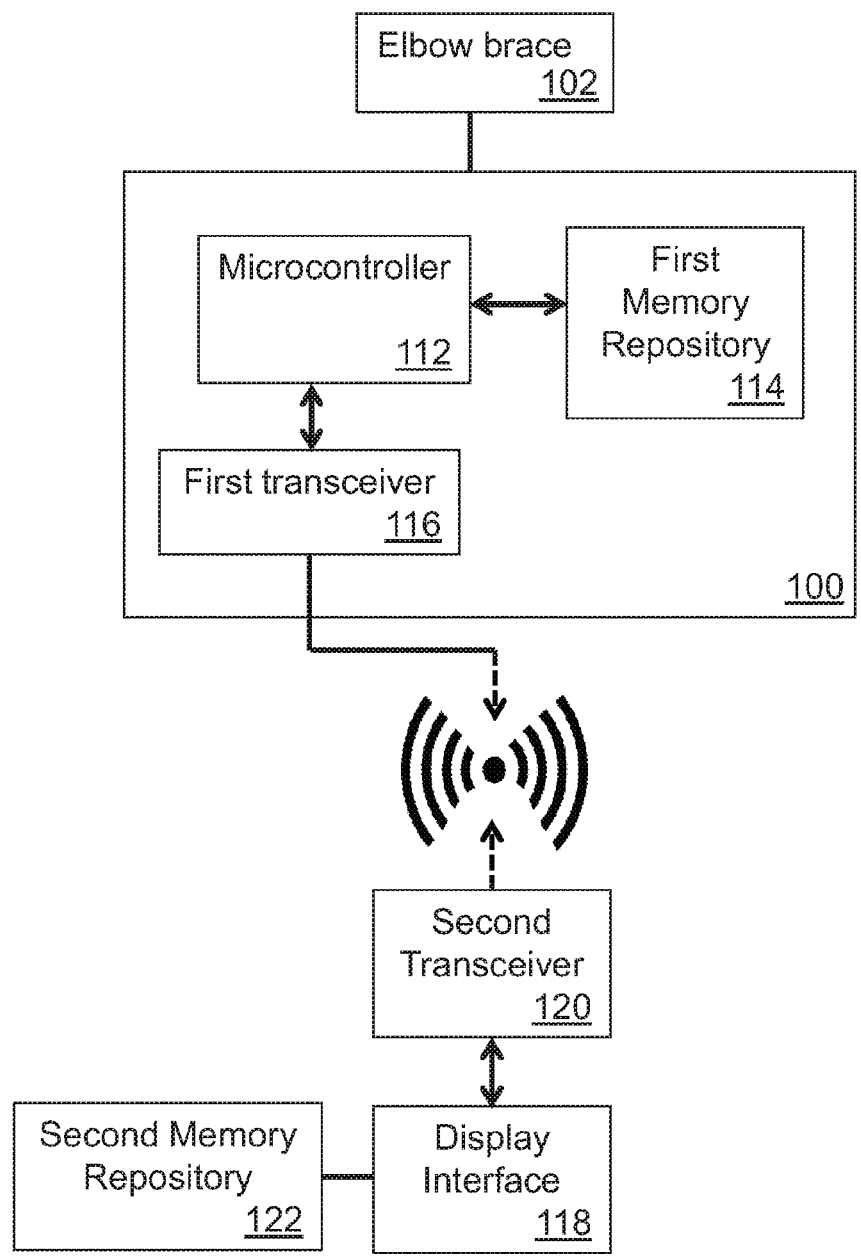
FIG. 10 show a block diagram of the communication components of the present invention.
Figure 11A:
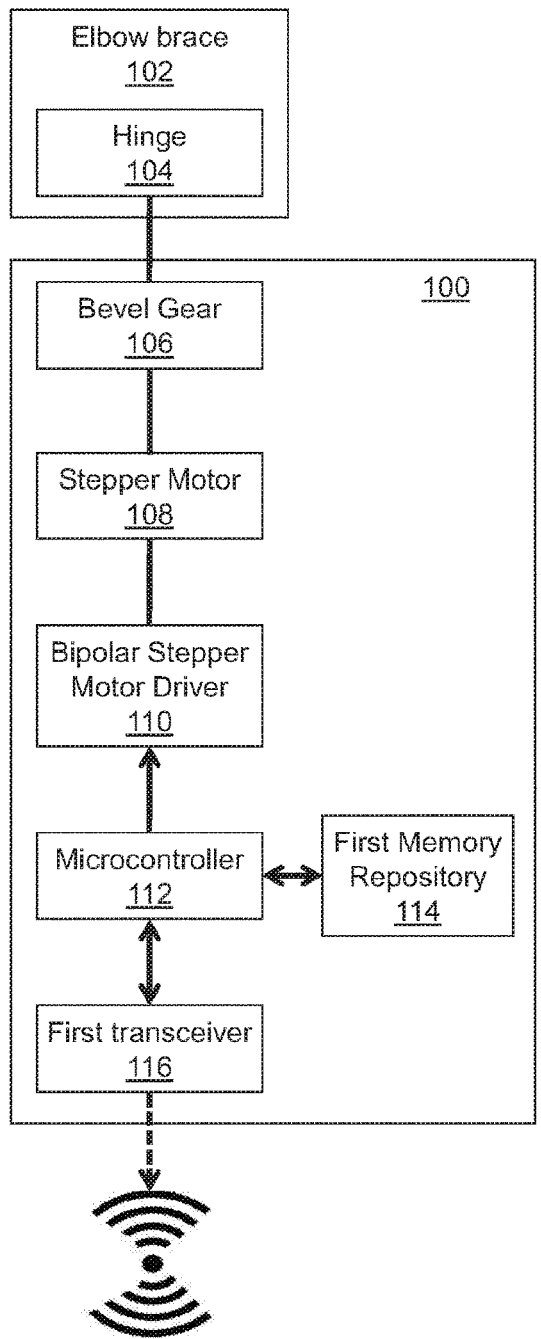
FIGS. 11A-11B show block diagrams of the present invention.
Figure 11B:
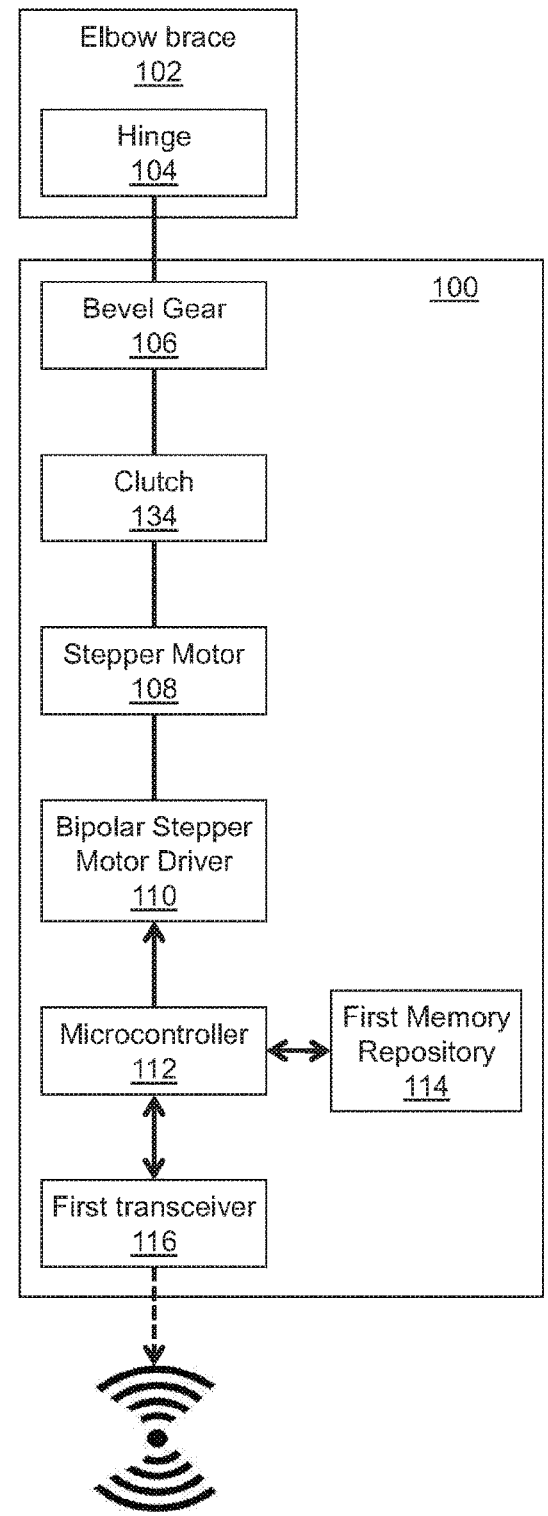
Figure 12:
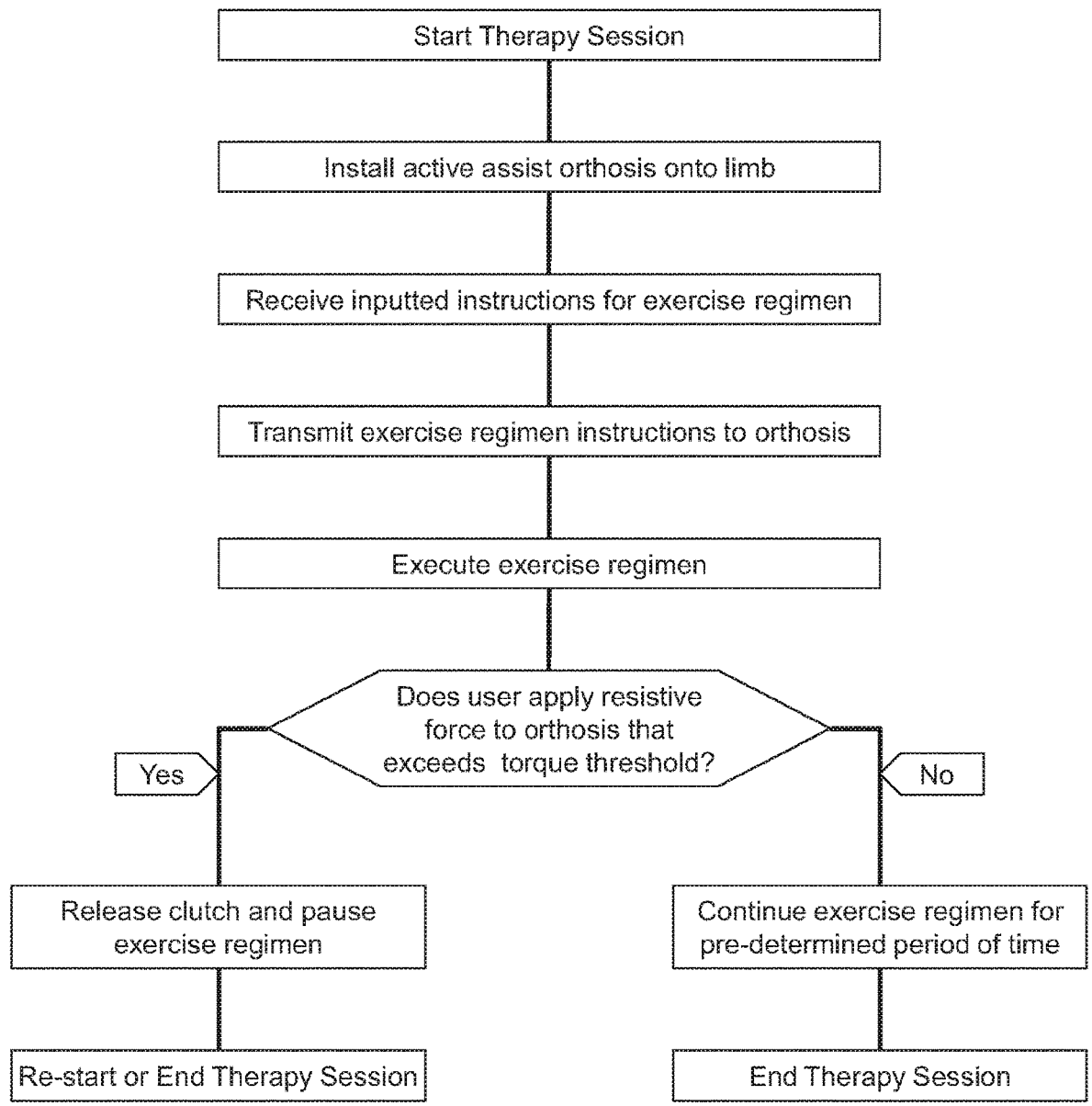
FIG. 12 shows a non-limiting scheme of a therapy regimen using the active assist orthotic of the present invention.

As shown in FIG. 9A, the Arduino® is the focal point of the arm brace electromechanical system. The Vcc pin on the Arduino® is connected to a 5 kilo-ohm potentiometer in series with a 1 kilo-ohm resistor. The ground ("GND") pin of the Arduino® is connected to the other side of the potentiometer-resistor series. In between the potentiometer and the resistor, the AO pin of the Arduino® reads the voltage at that node and converts it to a digital signal. The AO pin is a 12-bit analog to digital converter. The Arduino® reads the voltage between the resistor and potentiometer and converts that voltage to an angle reading with an equation, $V=88(\theta)/(1000+26.667\ \theta)$, describing the relationship between the voltage at the node between the resistor and potentiometer and the elbow angle. The angle reading is sent to the iOS® application through the Wi-Fi connection. A sampling rate for the ADO is 10,000 Hz, which is well above the minimum required sampling rate.

The Arduino® MKR1000 may be powered by the lithium ion polymer battery, which supplies 3.7 volts to the Vin pin of the Arduino®. The lithium ion polymer battery has 1200 mA-hours. Upon instruction from the iOS® application, the Arduino® connects 3.3 volts from pin 6 to control a bipolar stepper motor driver. The bipolar stepper motor is controlled by the Arduino® and powered by the 19.2 volt battery with 2000 mA-hours. The stepper motor driver drives the motor with the 19.2 volts from the battery. The motor has a 14:1 gearbox on its end to increase torque. The end of the gearbox interfaces with a clutch to prevent motor burnout. The clutch and motor interfaces with the elbow brace. Upon instruction from the Arduino®, the motor driver drives the motor, which adds torque at the elbow brace joint. The added torque aids the patient in flexion and extension of the arm.

In some embodiments, the brace may allow for extension control of −10 to 110 degrees and flexion control of 10 to 120 degrees. A plurality of straps may be attached to the brace which tighten around the arm and forearm. For example, two straps may be attached on the main frame of the brace and two straps may be connected to extending struts.

In one embodiment, a stepper motor may have an attached planetary gearbox with a 14:1 gear ratio. The motor can be powered with a battery of 12-24 volts. The maximum holding torque of the motor is 1.34 N-m and it requires a maximum current of 0.67 amperes to operate. Preferably, the motor weighs less than 1 lb to reduce the risk of injury while still delivering the necessary torque. In other embodiments, the motor driver may be a bipolar stepper motor driver that weighs less than 1 lb. The driver may be powered with a battery of 10-32 volts and has a maximum current output of 3 amperes.

In some embodiments, the clutch can have the following features: bidirectional performance and an adjustable maximum torque of 1.35 N-m (falling under the needed torque for the stepper motor). Without wishing to limit the invention to a particular mechanism, a clutch can ensure that external forces applied by the patient when performing exercises would not risk a stalling of the motor.

In one embodiment, the sensor is a 5K Ohm Linear Taper Rotary Potentiometer. When the knob on the potentiometer is turned, the resistance between the end terminals and the middle terminal changes. The potentiometer is a simple sensor because it can be assembled in a simple circuit that allows the Arduino to read the voltage between the potentiometer and the resistor. The voltage that will be read at node between the resistor and potentiometer is dependent on the resistance of the potentiometer. Because the resistance of the potentiometer changes with the turning of the knob, the potentiometer can be connected to the brace so that the knob turns with the elbow brace. The voltage read by the Arduino is therefore related to the elbow angle.

Figure 8:
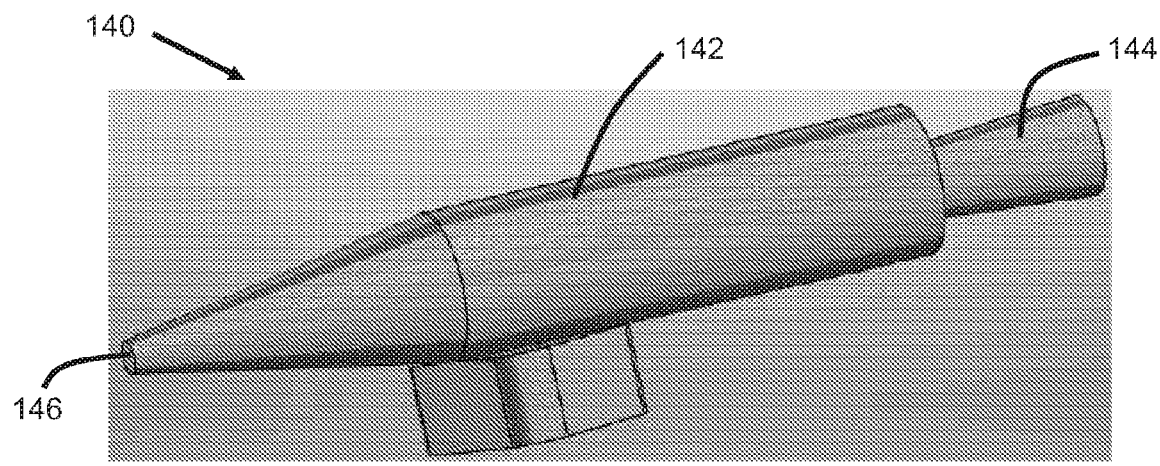
FIG. 8 shows an embodiment of the locking mechanism.

The locking mechanism is implemented in case the patient experiences any pain or discomfort. In one embodiment, as shown in FIG. 8, the mechanism comprises of a spring-action piece constructed to connect to the outer casing of the device. A locking pin will stay locked when pushed and then retract when pushed again. A bracket secures the piece to provide stability and allow it to latch onto the case at a point where the tip of the mechanism faces downward toward the gear of the brace. The pointed end thrusts into the main gear of the device and prevents it from rotating. The lock may be located in an easily accessible spot so that the patient can press it and the device will immediately stop extending or flexing. The locking mechanism is accessible to the patient in order to lock the elbow brace in place. The locking system is purely mechanical so that it is unaffected in the event of an electrical failure.

In some embodiments, the iOS® application can control the orthotic and there are several key features that are included in its programming. In a preferred embodiment, the application can communicate with the microcontroller.

There is a separate login feature for the patient and the physician. There is a calendar of the patient's scheduled exercises. The application contains a log of the patient's previous exercise history. The application contains a start and stop button for the patient to begin and end an exercise. A timer can track how long the patient has been doing a given exercise. In some cases, only the physician will be able to make changes to the exercise schedule of the patient via the physician login.

Presently, flexion and extension movement of the arm to prevent or decrease stiffness is guided by physical therapists or performed by patients at home. A level of risk (e.g. over-extension of the joint) is involved when patients perform these exercises alone and ease of access issues arise when a patient is wholly dependent on a physical therapist. As it has been described herein, the present invention transforms any elbow brace into an active assist orthotic allowing a user to independently exercise the elbow, with active assistance, according to a regimen designed by the patient's physician.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A hinged joint orthotic for providing assistance during active flexion or extension movement of a joint of a user to prevent or decrease joint stiffness, said flexion or extension movement comprising a plurality of angles, wherein each angle is a specified degree formed by a limb having the joint as a vertex, wherein the orthotic comprises:
   a. a first alignment plate (124);
   b. a second alignment plate (126) pivotably and operatively coupled to the first alignment plate (124) via a hinge (128);
   c. a bevel gear (106) disposed on the first alignment plate (124) at the hinge (128), said bevel gear (106) operatively coupled to the hinge (128); and
   d. a stepper motor (108) disposed on the first alignment plate (124) and aligned with the bevel gear (106), said stepper motor (108) having a motor shaft (136) operatively coupled to the bevel gear (106);

wherein the first alignment plate (124) and the second alignment plate (126) are configured to attach to a brace surrounding the user's limb, wherein the hinge (128) is positioned adjacent to the joint, wherein the alignment of the stepper motor (108) and the bevel gear (106) on the first alignment plate (124) positions the stepper motor (108) closer to a center of the limb and to a center of the user's body, thus reducing an apparent weight of the orthotic experienced by the user, wherein the stepper motor (108) applies a torque to the bevel gear (106), which transfers said torque to a gear shaft (132) of the bevel gear, wherein rotation of the shaft (132) drives rotation of the hinge (128), thereby moving the first alignment plate (124) and the second alignment plate (126) into a position reflecting the selected angle, wherein the brace moves simultaneously with the movement of the plates, thus positioning the limb at the selected angle.

2. The orthotic of claim 1 further comprising a gearbox (130) housing the bevel gear (106).

3. The orthotic of claim 1 further comprising a stepper motor driver (110) operatively coupled to the stepper motor (108).

4. The orthotic of claim 3 further comprising a microcontroller (112) operatively coupled to the stepper motor driver (110), wherein the microcontroller (112) activates the stepper motor driver (110) to drive the stepper motor (108) a number of motor steps required to position the brace at the selected angle.

5. The orthotic of claim 4 further comprising a memory repository, operatively coupled to the microcontroller (112), storing instructions comprising the number of motor steps required to position the active assist hinged joint orthotic at each angle.

6. The orthotic of claim 5, wherein the memory repository stores an exercise regimen comprising a series of angles to be executed by the user with aid from the active assist hinged joint orthotic.

7. The orthotic of claim 1 further comprising a clutch (134) operatively coupling the motor shaft (136) to the bevel gear (106), wherein if the limb of the user applies a resistance that opposes the movement of the brace, and thus the hinge (128), potentially leading to an opposing torque transfer damaging the stepper motor (108), then the clutch (134) is configured to release the motor shaft (136) to allow the motor shaft (136) to maintain its torque, wherein the opposing torque transferred to the bevel gear (106) is not experienced by the stepper motor (108) as a result of said clutch release.

8. An elbow orthotic for stabilizing an elbow of a user while providing assistance during active flexion or extension movement of an arm of the user to prevent stiffness or decrease stiffness of the elbow, the orthotic comprising:
   a. an elbow brace (102) comprising an upper component operatively coupled to a lower component via a first hinge (104), wherein the elbow brace (102) is configured to be worn on the arm such that an upper arm is disposed in the upper component, a forearm is disposed in the lower component, and the first hinge is adjacent to the elbow, wherein the first hinge permits flexion or extension movement of the arm from the elbow, said flexion or extension movement comprising a plurality of elbow angles, wherein each elbow angle is a specified degree formed by the elbow; and
   b. an active assist mechanism (100) comprising:
      i. a first alignment plate (124) operatively coupled to the upper component of the elbow brace (102);

ii. a second alignment plate (126) operatively coupled to the lower component of the elbow brace (102), wherein the second alignment plate (126) is pivotably coupled to the first alignment plate (124) via a second hinge (128) co-axial with the first hinge (104) and elbow;

iii. a bevel gear (106) disposed on the first alignment plate (124) at the hinge (128), said bevel gear (106) operatively coupled to the hinge (128); and iv. a stepper motor (108) disposed on the first alignment plate (124) and aligned with the bevel gear (106), said stepper motor (108) having a motor shaft (136) operatively coupled to the bevel gear (106);

wherein the alignment of the stepper motor (108) and the bevel gear (106) on the first alignment plate (124) positions the stepper motor (108) closer to a center of the arm and to a center of the user's body, thus reducing an apparent weight of the orthotic experienced by the user, wherein the stepper motor (108) is configured to apply a torque to the bevel gear (106), which transfers said torque to a gear shaft (132) of the bevel gear, wherein rotation of the shaft (132) drives rotation of the second hinge (128), thereby moving the first alignment plate (124) and the second alignment plate (126) into a position reflecting a selected angle of the plurality of elbow angles, wherein the elbow brace (102) moves simultaneously with the movement of the plates, thus positioning the arm at the selected angle, wherein the active assist mechanism (100) provides assistance to the user as the user exerts effort to move the arm to the selected elbow angle and wherein the elbow brace (102) stabilizes the elbow.

9. The orthotic of claim 8, wherein the active assist mechanism (100) further comprises a gearbox (130) housing the bevel gear (106).

10. The orthotic of claim 8, wherein the active assist mechanism (100) further comprises a clutch (134) operatively coupling the motor shaft (136) to the bevel gear (106), wherein rotation of the bevel gear (106) is synchronized to a rotation of the motor shaft (136) via the clutch (134), wherein if the limb of the user applies a resistance that opposes the movement of the brace, and thus the hinge (128), potentially leading to an opposing torque transfer damaging the stepper motor (108), then the clutch (134) is configured to release the motor shaft (136) to allow the motor shaft (136) to maintain its torque, wherein the opposing torque transferred to the bevel gear (106) is not experienced by the stepper motor (108) as a result of said clutch release.

11. The orthotic of claim 8, wherein the active assist mechanism (100) further comprises a stepper motor driver (110) operatively coupled to the stepper motor (108).

12. The orthotic of claim 11, wherein the active assist mechanism (100) further comprises:

a. a microcontroller (112) operatively coupled to the stepper motor driver (110);

b. a first memory repository (114) operatively coupled to the microcontroller (112) and storing instructions comprising a number of motor steps required to position the elbow brace (102) at each elbow angle; and c. a first transceiver (116) operatively coupled to the microcontroller (112);

wherein the microcontroller (112) activates the stepper motor driver (110) to drive the stepper motor (108) the number of motor steps required to position the elbow brace (102) at a selected elbow angle, thus applying a torque to the clutch (134) and consequently to the bevel gear (106), which applies the torque to the gear shaft (132).

13. The orthotic of claim 12, wherein the first transceiver (116) is wirelessly coupled to a second transceiver (120) that is operatively coupled to a display interface (118), wherein the display interface (118) receives an input indicating the selected elbow angle, wherein the second transceiver (120) wirelessly sends the input to the first transceiver (116) for subsequent transmission to the microcontroller (112), which activates the stepper motor driver (110) to ultimately rotate the second hinge (128) and move the alignment plates, and correspondingly the elbow brace (102), into the position reflecting the selected elbow angle.

14. The orthotic of claim 13, wherein the input is an exercise regimen comprising a series of elbow angles to be executed by the user within a given time period while being assisted by the active assist mechanism (100), wherein the given time period is clocked by a timer operatively coupled to the display interface (118).

15. The orthotic of claim 14, wherein the active assist mechanism (100) further comprises a potentiometer (138) that determines a degree of an elbow angle based on a position of the elbow brace (102), wherein the potentiometer (138) is coupled to the microcontroller (112), wherein the potentiometer (138) collects data comprising the degree of each elbow angle formed by the arm of the user and transmits said data to the microcontroller (112) for transmission, via the first transceiver (116), to the second transceiver (120), wherein the second transceiver (120) sends the data to the display interface (118) for display and subsequent storage in a second memory repository (122).

16. The orthotic of claim 14, wherein the display interface (118) is operatively coupled to a second memory repository (122) storing the exercise regimen.

17. The orthotic of claim 8, wherein the active assist mechanism (100) further comprises a DC power supply (111) to power the stepper motor (108).

18. The orthotic of claim 8, wherein the active assist mechanism (100) further comprises a locking mechanism (140) disposed on the elbow brace (102) adjacent to the first hinge (104) for locking the elbow brace (102) in a desired position, wherein the locking mechanism (104) comprises an inner tube (142) having a spring disposed therein, a pin (144) operatively coupled to a first end of the inner tube (142), and a conical tip (146) operatively coupled to a second end of the inner tube (142), wherein when the pin (144) is pressed, the pin (144) compresses the spring and locks in place, said spring compression thrusts the conical tip (146) into a gear disposed within the first hinge (104), thereby preventing the gear, and thus the elbow brace (102), from rotating, wherein the pin (144) is pressed again to release the pin (144) from its locked configuration, which causes the pin (144) to retract from the inner tube (142), thereby releasing the spring and causing retraction of the conical tip (146), thus freeing the gear and the elbow brace (102) to allow rotation thereof.

19. A method for providing active assistance to an arm of a user performing flexion or extension movement in order to prevent or decrease stiffness of an elbow joint, said flexion or extension movement comprising a plurality of elbow angles, each elbow angle is a specified degree formed by the elbow, wherein the method comprises:

a. providing an orthotic according to claim 8;

b. installing the elbow brace (102) onto the arm such that an upper arm is disposed in the upper component, a forearm is disposed in the lower component, and the first hinge (104) is adjacent to the elbow; and c. driving the stepper motor (106) a number of motor steps required to position the elbow brace (102) at a selected elbow angle of the plurality of elbow angles, thus applying a torque to the bevel gear (106) via a motor shaft (136), which transfers said torque to a gear shaft (132) of the bevel gear, wherein rotation of the shaft (132) drives rotation of the second hinge (128), thereby moving the first alignment plate (124) and the second alignment plate (126) into a position reflecting the selected angle, wherein the elbow brace (102) moves simultaneously with the movement of the plates, thus positioning the arm at the selected angle, wherein the active assist mechanism (100) assists the user as the user exerts effort to move the arm to the selected elbow angle.

20. The method of claim 19, wherein the active assist mechanism (100) of the orthotic further comprises a clutch (134) operatively coupling the motor shaft (136) to the bevel gear (106), wherein rotation of the bevel gear (106) is synchronized to a rotation of the motor shaft (136) via the clutch (134), wherein if the user applies a resistance that opposes the movement of the elbow brace (102), and thus the hinge (128), potentially leading to an opposing torque transfer damaging the stepper motor (108), then the clutch (134) is configured to release the motor shaft (136) to allow the motor shaft (136) to maintain its torque, wherein the opposing torque transferred to the bevel gear (106) is not experienced by the stepper motor (108) as a result of said clutch release.

\* \* \* \* \*